United States Patent [19]

Suzukamo et al.

[11] Patent Number: 4,820,864
[45] Date of Patent: Apr. 11, 1989

[54] METHOD FOR RACEMIZATION OF OPTICALLY ACTIVE CHRYSANTHEMIC ACID OR ITS ESTER

[75] Inventors: Gohfu Suzukamo, Osaka; Yoji Sakito, Hyogo; Masami Fukao, Osaka, all of Japan

[73] Assignee: Sumitomo Chemical Company, Limited, Osaka, Japan

[21] Appl. No.: 166,014

[22] Filed: Mar. 9, 1988

[30] Foreign Application Priority Data

Mar. 9, 1987 [JP] Japan ................................ 62-533519
Mar. 26, 1987 [JP] Japan ................................ 62-73355
Jun. 10, 1987 [JP] Japan ................................ 62-145467

[51] Int. Cl.$^4$ ............................................. C07C 51/353
[52] U.S. Cl. ..................................... 560/124; 562/401; 562/506
[58] Field of Search ................. 560/124; 562/401, 506

[56] References Cited

U.S. PATENT DOCUMENTS

| | | | |
|---|---|---|---|
| 3,282,984 | 11/1966 | Matsui et al. | 260/468 |
| 3,657,086 | 4/1972 | Matsui et al. | 204/158 R |
| 3,989,750 | 11/1976 | Nagase et al. | 260/544 |
| 4,182,906 | 1/1980 | Suzukamo et al. | 562/506 |
| 4,473,703 | 9/1984 | Suzukamo | 560/124 |
| 4,485,257 | 11/1984 | Suzukamo et al. | 562/401 |
| 4,644,080 | 2/1987 | Suzukamo et al. | 560/124 |
| 4,659,864 | 4/1987 | Suzukamo et al. | 560/124 |
| 4,723,035 | 2/1988 | Suzukamo | 560/124 |

FOREIGN PATENT DOCUMENTS 0061880 10/1982 European Pat. Off. .
0155765 9/1985 European Pat. Off. .
0165070 12/1985 European Pat. Off. .
0235940 9/1987 European Pat. Off. .

*Primary Examiner*—Michael L. Shippen
*Attorney, Agent, or Firm*—Birch, Stewart, Kolasch & Birch

[57] ABSTRACT

Racemization of an optically active chrysanthemic acid or its ester of the formula:

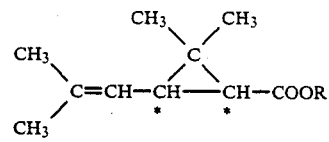

wherein R represents a hydrogen atom, an alkyl group of 1–20 carbon atoms, a cycloalkyl group of 3–20 carbon atoms or an aralkyl group of 7–20 carbon atoms and * mark indicates asymmetric carbon atom, is effected by contacting the acid or its ester with at least one compound selected from the group consisting of a carboxylic acid bromide, a silicon bromide, an S-bromine compound, and N-bromine compound, a halo-bromine compound and an SH compound in the presence of a peroxide or an azo compound.

18 Claims, No Drawings

METHOD FOR RACEMIZATION OF OPTICALLY ACTIVE CHRYSANTHEMIC ACID OR ITS ESTER

The present invention relates to a method for preparing racemized chrysanthemic acid or its ester. More particularly, the invention relates to a method for preparing racemized chrysanthemic acid or its esters by treating optically active chrysanthemic acid or its ester of the formula:

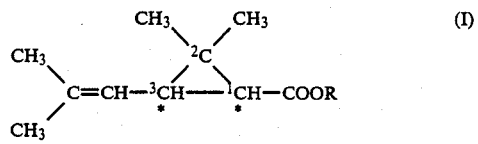

(wherein R represents a hydrogen atom, an alkyl group of 1–20 carbon atoms, a cycloalkyl group of 3–20 carbon atoms or an aralkyl group of 7–20 carbon atoms and * mark shows asymmetric carbon atom), which comprises contacting with at least one compound selected from carboxylic acid bromides, silicon bromides, S-bromine compounds, N-bromine compounds, halo-bromine compounds and SH compounds in the presence of a peroxide or an azo compound.

Chrysanthemic acid constitutes an acid component of esters well-known as so-called pyrethroid insecticides, such as pyrethrin, allethrin, phthalthrin, etc., which are utilized as low mammalian toxic, quickly effective insecticides, and the chrysanthemic acid or its ester represented by the above formula (I) is useful as an intermediate of these esters.

The chrysanthemic acid represented by the above formula (I) has four isomers, that is, two geometrical isomers, i.e. cis and trans forms, each of which respectively has two optical isomers, i.e. (+) and (−) forms. It has been known that, in general, among the isomers the esters composed of the trans-form acid exhibit stronger insecticidal activity than those composed of the corresponding cis-form acid, and furthermore, the esters composed of (+)-form acid exhibit exceedingly higher activity than those composed of the corresponding (−)-isomer.

In general, chrysanthemic acid is industrially produced as a mixture of cis and trans forms, each of which is in the form of racemic modification, namely, as (±)-form. Optical resolution of the thus-synthesized acid by means of an optically active organic base is conducted to obtain the (+)-form acid which is utilized for the preparation of insecticidal compounds with a higher activity. The remaining (−)-isomer is not very useful, since the esters composed thereof are almost inactive. Accordingly, it is a problem to be solved in the production of the (+)-form acid, particularly on a commercial scale, that the (−)-form acid should be racemized with a high efficiency, so as to be utilized again as the material for the optical resolution mentioned above.

Racemization of optically active chrysanthemic acid represented by the formula (I) is difficult, since it possesses two asymmetric carbon atoms exhibited by * marks, as shown above, at the 1- and 3-positions of the cyclopropane.

Some methods for racemization have so far been studied. The methods known are a method in which (−)-trans-chrysanthemic acid is oxydized at its $C_3$-substituted isobutenyl group to convert it to a ketoalcohol group, and the acid group at the $C_1$-position is converted to a lower alkyl ester, which is then subjected to a reaction with an alkali metal alcoholate in a solvent (U.S. Pat. No. 3,282,984); a method in which (−)-trans-chrysanthemic acid is irradiated with ultraviolet rays in the presence of a photosensitizer (U.S. Pat. No. 3,657,086). The former requires many reaction steps, and the latter is inferior in reactivity and consumes a large quantity of electric power of the light source. Thus, there are various problems to be solved for industrial application.

The inventors proposed the following methods: a method in which optically active chrysanthemic acid is converted to the corresponding acid halide and then contacted with a Lewis acid (U.S. Pat. Nos. 3,989,750 and 4,182,906); a method in which optically active chrysanthemic acid is converted to acid anhydride and then contacted with iodine (U.S. Pat. No. 4,485,257); and a method in which chrysanthemic acid is allowed to contact with a specific catalyst, boron bromide or aluminum bromide in the presence or absence of a peroxide (U.S. Pat. Nos. 4,644,080 and 4,659,864).

After an extensive study, the inventors have found that racemization of optically active chrysanthemic acid or ester thereof having the formula (I) proceeds by bringing it into contact with at least one compound selected from carboxylic acid bromides, silicon bromides, S-bromine compounds, N-bromine compounds, halo-bromine compounds and SH compounds in the presence of a peroxide or an azo compound. The present invention has been established on the basis of such finding and additional research.

According to the present invention, the optically active chrysanthemic acid or its ester is readily able to be racemized in high yield. The method of the present invention is very convenient for racemization, particularly, on a commercial scale. Moreover, the present invention enables direct utilization, with high efficiency, of (−)-chrysanthemic acid or its ester, which is separated off in the procedures of optical resolutions, without conversion into other derivatives.

The present invention is advantageous because the racemic mixture obtained is rich in trans isomer which is more effective. Thus, the present process is also applied to the conversion of racemic cis isomer or racemic mixture of cis and trans isomers of chrysanthemic acid into the corresponding racemic trans-rich isomer.

The method of the present invention will more fully be described hereinafter.

In the present invention, any of the four optical isomers of chrysanthemic acid or its ester is used solely or in mixtures of isomers as the starting material. Namely, the starting material of any degree of optical purity is employed. Needless to say, however, it is preferred to use, as the starting material, the (−)-form or one rich in the (−)-form.

As the optically active chrysanthemic acid or ester represented by the formula (I) mention may be made of, for example, chrysanthemic acid, methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

Carboxylic acid bromides, a catalyst in the present invention, are usually those having 1–18 carbon atoms. They include, for example, aliphatic carbonyl bromides such as acetyl bromide, propionyl bromide, butyryl bromide, isobutyryl bromide, valeryl bromide, isovaleryl bromide, pivaloyl bromide, hexanoyl bromide, heptanoyl bromide, cyclohexanecarbonyl bromide, octanoyl bromide, nonanoyl bromide, decanoyl bromide, 3-(2-methylpropenyl)-2,2-dimethylcyclopropanecarbonyl bromide, undecanoyl bromide, palmitoyl bromide and stearoyl bromide; aliphatic dicarboxylic acid dibromides such as malonyl dibromide, succinyl dibromide, glutaryl dibromide, adipoyl dibromide, pimeloyl dibromide, suberoyl dibromide, azelaoyl dibromide and sebacoyl dibromide; acid bromides of mono and dicarboxylic acids having aromatic group such as benzoyl bromide, phenylacetyl bromide, phenylpropionyl bromide, phenylbutyryl bromide, naphthalenecarbonyl bromide, phthaloyl dibromide, terephthaloyl dibromide and isophthaloyl dibromide.

Examples of the silicon bromides used as a catalyst are lower alkylsilyl bromides such as trimethylsilyl bromide, dimethylsilyl dibromide, methylsilyl tribromide and triethylsilyl bromide and silyl tetrabromide.

N-bromine compounds used as a catalyst are, for example, N-bromosuccinimide, N-bromoacetamide, N-bromopropionamide, N-bromobutyramide and N-bromovaleramide.

S-bromine compounds used as a catalyst are, for example, thionyl bromide, sulfuryl bromide, p-toluenesulfonyl bromide, arylsulfinyl bromides such as phenylsulfinyl bromide and lower alkylsulfonyl bromides such as methanesulfonyl bromide.

Halo-bromine compounds used as a catalyst are, for example, bromine, iodine monobromide and iodine tribromide.

SH compounds used as a catalyst in the present invention may be any of those containing -SH group. Thiols, carbothioic acids and carbodithioic acid are usually used. They are, for example, aromatic thiols such as thiophenol, o-, m- and p-thiocresols, o-, m- and p-methoxybenzene thiols, 1- and 2-naphthalenethiols and thiosalicylic acid; aralkylthiols such as benzyl mercaptane; aliphatic thiols such as methanethiol, ethanethiol, 1-propanethiol, 2-propanethiol, butanethiol, pentanethiol, hexanethiol, heptanethiol, octanethiol, nonanethiol, decanethiol, dodecanethiol, thioglycolic acid, thiolactic acid and thiomalic acid; polythiols such as dithiocatechol, dithioresorcin, dithiohydroquinone, dithiothritol, ditioerythritol and butanedithiol; thiocarboxylic acids such as thioacetic acid, thiopropionic acid, thiobutyric acid and thiobenzoic acid and dithio acids such as dithioacetic acid, dithiopropionic acid, dithiobutyric acid and dithiobenzoic acid. Preferred compounds are carboxylic acid bromides, halo-bromine compounds, silicon bromides and aromatic thiols.

Compounds to be used as a cataylst are used in an amount within the range of 1/1000–¼ mol, preferably 1/200–1/6 mol per 1 mol of chrysanthemic acid or ester thereof.

These catalysts are employed together with co-catalysts such as peroxides and azo compounds.

Peroxides are, for example, hydroperoxides such as t-butyl hydroperoxide, 1,1,3,3-tetramethylbutyl hydroperoxide, cumene hydroperoxide, diisopropylbenzene hydroperoxide, etc., hydroperoxides produced by oxidation of ethers such as tetrahydrofuran, dioxane, etc., diacyl peroxides such as benzoyl peroxide, lauroyl peroxide, etc., peroxy esters such as t-butyl perbenzoate, t-butyl peracetate, diisopropyl peroxydicarbonate, dicyclohexyl peroxydicarbonate, etc., ketone peroxides such as methyl ethyl ketone peroxide, cyclohexanone peroxide, etc., dialkyl peroxides such as di-t-butyl peroxide, dicumyl peroxide, etc., peracids such as peracetic acid, etc., hydrogen peroxide, etc. Of these peroxides, preferred are diacyl peroxides, peroxy esters and hydroperoxides, more preferred diacylperoxides and peroxy esters.

The peroxide is used usually in an amount of 1/20–5 mol, preferably 1/10–2 mol per mol of the catalyst.

Azo compounds include azonitriles such as azobisisobutylonitrile, 2,2'-azobis(2,4-dimethylvaleronitrile), 1,1'-azobis(cyclohexane-1-carbonitrile), 4,4'-azobis-4-cyanopentanoic acid, 2-phenylazo-2,4-dimethyl-4-methoxyvaleronitrile and 2-cyano-2-propylazoformamide; azo-esters such as methyl azobisisobutyrate and ethyl azobisisobutyrate and alkylazo compounds such as azo-t-butane. Azo-nitriles and azo-esters are preferable.

The azo compound is usually used, in an amount from 1/10 to 5 mol, preferably ¼ to 2 mol, per mol of the catalyst.

The present racemization reaction is preferably carried out in the presence of an inert solvent. The solvents include saturated aliphatic hydrocarbons, aromatic hydrocarbons and their halide compounds, ethers, etc.

The reaction temperature varies depending on the catalyst and co-catalyst employed. The temperature ranges usually from $-30°$ C. to boiling point of the chrysanthemic acid or its ester or boiling point of the solvent when it is employed. The temperature is usually $-20°$ C. to 100° C.

The reaction time varies depending on the amounts and varieties of the catalyst and co-catalyst employed and reaction temperature, too, but usually ranges from a few minutes to 10 hours.

In carrying out the method of the present invention, for example, the chrysanthemic acid or esters thereof is mixed with the co-catalyst in the presence of a solvent, and thereto is added the catalyst; or the chrysanthemic acid or esters thereof is dissolved in a solvent and then thereinto are added in parallel the catalyst together with co-catalyst.

The racemized chrysanthemic acid or ester thus obtained is reused as a starting material for optical resolution or as an intermediate for insecticidal esters.

Moreover, the racemization method of the present invention can be also applied to the conversion of the racemic cis isomer or of a mixture of the cis and trans isomers of chrysanthemic acid or its ester to more useful corresponding racemic trans-rich isomer.

The following examples will further explain the present invention.

EXAMPLE 1

271 mg of (−)-trans-chrysanthemic acid was dissolved in 10 ml of benzene, followed by adding 13 mg of azobisisobutyronitrile. Thereto was added dropwise a solution of bromine (12 mg) in carbon tetrachloride at 80° C. over a period of 10 minutes with stirring. After 15 minutes, the reaction mixture was washed with dilute aqueous hydrochloric acid. To the organic layer was added 5.0 g of a 10% aqueous sodium hydroxide solution with stirring at about 40° C.

The separated aqueous layer was neutralized with dilute sulfuric acid and extracted with toluene and then the toluene layer was washed with water. The toluene solution was concentrated and then distilled to obtain 260 mg of distillate having a boiling point of 110°–119° C./2.5 mmHg. The IR spectrum of the product was identical with that of chrysanthemic acid. A part of the distillate was converted into (+)-2-octyl ester, which was subjected to measurement of optical isomer ratio by gas chromatography to give the following results: (+)-cis, 3.0%; (−)-cis, 3.2%; (+)-trans, 44.7%; and (−)-trans, 49.1%

EXAMPLE 2

500 mg of (-)-cis-chrysanthemic acid was dissolved in 10 ml of toluene, followed by adding 20 mg of azobisisobutyronitrile. Thereto was added dropwise a solution of bromine (19 mg) in carbon tetrachloride at 80° C. over a period of 10 minutes with stirring. After 15 minutes, the reaction mixture was subjected to a treatment similar to Example 1 to obtain 452 mg of chrysanthemic acid. The optical isomer ratio was as follows: (+)-cis, 3.3%; (−)-cis, 3.2%; (+)-trans, 47.0%; and (−)-trans, 46.5%.

EXAMPLE 3

10.0 g of (-)-chrysanthemic acid (composition: (+)-cis, 1.8%; (−)-cis, 17.6%; (+)-trans, 10.1%; and (−)-trans 70.5%) was dissolved in 20 ml of toluene, followed by adding 97 mg of azobisisobutyronitrile. Thereto was added dropwise a solution of bromine (0.48 g) in carbon tetrachloride with stirring at 80° C. over a period of 15 minutes. Then, a procedure similar Example 1 was carried out to obtain 8.73 g of chrysanthemic acid. The optical isomer ratio was as follows: (+)-cis, 3.1%; (−)-cis, 3.2%; (+)-trans, 44.5%; and (−)-trans, 49.2%.

EXAMPLE 4

In a 100 ml flask were charged 10.0 g of the same chrysanthemic acid as used in Example 3, 20 ml of toluene and 0.58 g of t-butyl perbenzoate under nitrogen. Tnereto was added dropwise a solution of bromine (0.58 g) in carbon tetrachloride with stirring at 100° C. and, the reaction mixture was stirred at same temperature for 20 minutes. After the similar post-treatment of Example 1 of the reaction mixture, it was distilled to obtain 8.1 g of chrysanthemic acid. Optical isomer ratio thereof was as follows: (+)-cis, 3.3%; (−)-cis, 3.3%; (+)-trans, 44.5%; and (−)-trans, 48.9%.

EXAMPLE 5 10.0 g of the same chrysanthemic acid as used in Example 3 and 0.24 g of azobisisobutyronitrile were dissolved in 20 ml of chlorobenzene, followed by adding dropwise a solution of bromine (0.48 g) in carbon tetrachloride with stirring at 80° C.

After 15 minutes, a treatment similar to Example 1 was effected to obtain 8.2 g of chrysanthemic acid. Optical isomer ratio was as follows: (+)-cis; 3.1%; (−)-cis, 3.1%; (+)-trans, 46.0%; and (−)-trans, 47.8%.

EXAMPLE 6

Example 5 was repeated except that dioxane was used as a reaction solvent in place of chlorobenzene to obtain 8.1 g of chrysanthemic acid. Optical isomer ratio thereof was as follows: (+)-cis, 3.1%; (−)-cis, 3.1%; (+)-trans, 44.4%; and (−)-trans, 49.4%.

EXAMPLE 7 10.0 g of the same chrysanthemic acid as used in Example 3 and 0.31 g of benzoyl peroxide were dissolved in 20 ml of toluene and thereto was added dropwise a solution of bromine (0.95 g) in carbon tetrachloride with stirring at 80° C.

After 15 minutes, the similar a post-treatment similar Example 1 was effected to obtain 8.2 g of chrysanthemic acid. Optical isomer ratio thereof was as follows: (+)-cis, 3.3%; (−)-cis, 3.3%; (+)-trans, 44.4%; and (−)-trans, 49.0%.

EXAMPLE 8

In a 100 ml flask were charged 5.0 g of ethyl chrysanthemate (composition: (+)-cis, 1.8%; (−)-cis, 18.3%; (+)-trans, 11.1%; and (−)-trans, 68.8%), 20 ml of toluene and 0.49 g of benzoyl peroxide under nitrogen and thereto was added dropwise a solution of bromine (0.41 g) in carbon tetrachloride with stirring at 80° C.

After 0.5 hour, the reaction mixture was washed with a 2% aqueous sodium hydroxide solution and water. The organic layer was concentrated under reduced pressure and distilled to obtain 4.1 g of a distillate having a boiling point of 85°–88° C./10 mmHg.

The IR spectrum of the product was identical with that of ethyl chrysanthemate. A part of the product was hydrolyzed by a conventional method to obtain a carboxylic acid. Gas chromatographic assay of the carboxylic acid gave the following optical isomer ratio: (+)-cis, 3.8%; (−)-cis, 3.8%; (+)-trans, 44.8%; and (−)-trans, 47.5%.

EXAMPLE 9

10.0 g of the same (−)-chrysanthemic acid as used in Example 3 was dissolved in 20 ml of toluene. Thereto was added 0.19 g of azobisisobutyronitrile with stirring at 80° C., and added dropwise 0.18 g of acetyl bromide.

After 15 minutes, a treatment similar to Example 1 was effected to obtain 9.34 g of chrysanthemic acid. Optical isomer ratio thereof was as follows: (+)-cis, 3.5%; (−)-cis, 3.5%; (+)-trans, 44.3%; and (−)-trans, 48.7%.

EXAMPLE 10

To 10.0 g of the same chrysanthemic acid as used in Example 3 were added 20 ml of toluene and 0.58 g of t-butyl perbenzoate, and thereto was added dropwise a solution of acetyl bromide (0.37 g) in carbon tetrachloride with stirring at 100° C., and the solution was kept stirring at the same temperature for 20 minutes.

After a post-treatment similar to Example 1 of the reaction mixture, it was distilled to obtain 8.3 g of chrysanthemic acid. Optical isomer ratio thereof was as follows: (+)-cis, 3.4%; (−)-cis, 3.6%; (+)-trans, 44.5%; and (−)-trans, 48.5%.

EXAMPLE 11

4.00 g of the same chrysanthemic acid as used in Example 3 was dissolved in 20.0 ml of toluene. Thereto was added 98 mg of azobisisobutyronitrile and then was added dropwise 91 mg of trimethylsilyl bromide with stirring at 80° C.

Then, the same treatment as in Example 1 was effected to obtain 3.68 g of chrysanthemic acid. Optical isomer ratio thereof was as follows: (+)-cis, 3.5%; (−)-cis, 3.5%; (+)-trans, 45.4%; and (−)-trans, 47.6%.

EXAMPLE 12

2.00 g of the same chrysanthemic acid as used in Example 3 was dissolved in 10.0 ml of chlorobenzene and thereto was added 0.23 g of t-butyl perbenzoate, followed by adding dropwise 87 mg of trimethylsilyl bromide with stirring at 100° C.

Then, a post-treatment similar to Example 1 was effected to obtain 1.63 g of chrysanthemic acid. Optical isomer ratio was as follows: (+)-cis, 3.8%; (−)-cis, 3.9%; (+)-trans, 45.1%; and (−)-trans, 47.2%.

EXAMPLE 13

2.1 g of the same chrysanthemic acid as used in Example 3 was dissolved in 10 ml of toluene, followed by adding 0.11 g of t-butyl hydroperoxide. Thereto was added 0.19 g of trimethylsilyl bromide at 20° C. with stirring, and the reaction mixture was stirred at the same temperature for 20 minutes.

Then, a post-treatment similar to Example 1 was effected to obtain 1.9 g of chrysanthemic acid. Optical isomer ratio thereof was as follows: (+)-cis, 2.1%; (−)-cis, 2.1%; (+)-trans, 46.3%; and (−)-trans, 49.5%.

EXAMPLE 14

0.50 g of (−)-cis-chrysanthemic acid and 47 mg of azobisisobutyronitrile were dissolved in 10 ml of toluene. Thereto was added dropwise 59 mg of thionyl bromide with stirring at 80° C., and the solution was stirred at the same temperature for 20 minutes.

Then, a post-treatment similar to Example 1 was effected to obtain 0.4 g of chrysanthemic acid. Optical isomer ratio thereof was as follows: (+)-cis, 3.6%; (−)-cis, 7.1%; (+)-trans, 44.8%; and (−)-trans, 44.5%.

EXAMPLE 15

1.0 g of the same chrysanthemic acid as used in Example 3 and 98 mg of azobisisobutyronitrile were dissolved in 10 ml of dioxane. Thereto was added 0.15 g of N-bromosuccinimide with stirring at 80° C. and the solution was kept stirring at the same temperature for 20 minutes.

Then, 1 g of a 40% aqueous sodium hydroxide solution was added to the reaction mixture and the solvent was distilled off under reduced pressure. To the residue was added water and the product was extracted with toluene. The aqueous layer was acidified with dilute sulfuric acid and extracted with toluene and then washed with water. The organic layer was concentrated and distilled to obtain 0.79 g of chrysanthemic acid. (Boiling point: 110°–119° C./2.5 mmHg). Optical isomer ratio was as follows: (+)-cis, 2.1%; (−)-cis, 2.1%; (+)-trans, 40.6%; and (−)-trans, 55.2%.

EXAMPLE 16

1.0 g of the same chrysanthemic acid as used in Example 3 and 98 mg of azobisisobutyronitrile were dissolved in 10 ml of toluene. Thereto was added dropwise 0.11 g of benzoyl bromide with stirring at 80° C., and the reaction mixture was stirred for 20 minutes at the same temperature as above.

Optical isomer ratio of the product was as follows: (+)-cis, 3.3%; (−)-cis, 2.4%; (+)-trans, 43.6%; and (−)-trans, 50.7%.

EXAMPLE 17

2.0 g of the same chrysanthemic acid as used in Example 3 and 0.15 g of azobisisobutyronitrile were dissolved in 20 ml of toluene. Thereto was added dropwise 0.25 g of adipoyl dibromide with stirring at 80° C. and the solution was kept stirring at the same temperature as above for 20 minutes.

Optical isomer ratio of the product was as follows: (+)-cis, 3.8%; (−)-cis, 3.4%; (+)-trans, 43.4%; and (−)-trans, 49.4%.

EXAMPLE 18

3.2 g of the ethyl chrysanthemate used in Example 8 and 0.27 g of azobisisobutyronitrile were dissolved in 20 ml of toluene. Thereto was added 0.38 g of trimethylsilyl bromide with stirring at 80° C. and the reaction mixture was kept stirring at the same temperature as above for 20 minutes. Then, a post-treatment similar to Example 8 was effected to obtain 2.6 g of ethyl chrysanthemate. Optical isomer ratio was as follows: (+)-cis, 3.5%; (−)-cis, 3.5%; (+)-trans, 43.5%; and (31)-trans, 49.5%.

EXAMPLE 19

0.32 g of the same ethyl chrysanthemate as used in Example 8 and 50 mg of benzoyl peroxide were dissolved in 10 ml of chlorobenzene. Thereto was added 29 mg of acetyl bromide at 80° C. and, the solution was kept stirring at the same temperature for 20 minutes.

A part of the reaction product was hydrolyzed by a conventional method and optical isomer ratio thereof was determined to obtain the following results: (+)-cis, 3.5%; (−)-cis, 3.5%; (+)-trans, 42.0%; and (−)-trans, 51.0%.

EXAMPLE 20

1.0 g of (−)-cis-chrysanthemic acid and 48 mg of azobisisobutyronitrile were dissolved in 5 ml of toluene. Thereto was added dropwise a solution of thiophenol (55 mg) in toluene with stirring at 80° C., followed by further stirring for 30 minutes at the same temperature.

Then, the reaction mixture was washed with dilute aqueous hydrochloric acid. The organic layer was extracted twice with 5 g of a 10% aqueous sodium hydroxide solution and the aqueous layer was acidified with hydrochloric acid and extracted twice with toluene. The toluene layer was washed with water and dried over sodium sulfate and then the solvent was distilled off under reduced pressure. Then, the residue was distilled to obtain 0.92 g of a distillate having a boiling point of 110°–119° C./2.5 mmHg. The IR spectrum of the product was identical with that of chrysanthemic acid.

Optical isomer ratio thereof was determined by gas chromatography to obtain the following results: (+)-cis, 3.8%; (−)-cis, 6.7%; (+)-trans, 44.7%; and (−)-trans, 44.8%.

EXAMPLE 21

1.0 g of (−)-chrysanthemic acid (composition: (+)-cis, 1.8%; (−)-cis, 17.6%; (+)-trans, 10.1%; and (−)-trans, 70.5%) and 0.11 g of t-butyl perbenzoate were dissolved in 5 ml of toluene. Thereto was added dropwise a solution of thiophenol (110 mg) in toluene, followed by further stirring for 30 minutes at the same temperature.

Then, a treatment similar to Example 20 was effected to obtain 0.89 g of chrysanthemic acid.

Optical isomer ratio was as follows: (+)-cis, 6.9%; (−)-cis, 7.0%; (+)-trans, 41.5%; and (−)-trans, 44.6%.

EXAMPLE 22

In a 100 ml flask, under nitrogen, 1.31 g of ethyl chrysanthemate (composition: (+)-cis, 1.8%; (−)-cis, 18.3%; (+)-trans, 11.1%; and (−)-trans, 68.8%) and 82 mg of azobisisobutyronitrile were dissolved in 5 ml of toluene. Thereto was added dropwise a solution of thiophenol (110 mg) in toluene with stirring at 80° C., followed by stirring for 30 minutes at the same temperature.

Then, the reaction mixture was washed with a 2% aqueous sodium hydroxide solution and water. The organic layer was concentrated under reduced pressure and then, distilled to obtain 1.17 g of a distillate having a boiling point of 85°–88° C./10 mmHg. The IR spectrum of the distillate was identical with that of ethyl chrysanthemate. A part of the distillate was hydrolyzed by conventional method to obtain a carboxylic acid. Gas chromatographic assay of the carboxylic acid gave the following optical isomer ratio: (+)-cis, 4.3%; (−)-cis, 4.4%; (+)-trans, 44.9%; and (−)-trans, 46.4%.

EXAMPLE 23

1.31 g of the same ethyl chrysanthemate as used in Example 22 and 0.12 g of t-butyl perbenzoate were dissolved in 5 ml of toluene and thereto was added dropwise a solution of thiophenol (110 mg) in toluene with stirring at 90° C., and the reaction mixture was strred for 30 minutes at the same temperature.

Optical isomer ratio thereof was as follows: (+)-cis, 6.1%; (−)-cis, 6.2%; (+)-trans, 43.4%; and (−)-trans, 44.3%.

EXAMPLE 24

500 mg of (-)-cis-chrysanthemic acid and 48 mg of azobisisobutyronitrile were dissolved in 5 ml of toluene and thereto was added dropwise a solution of p-thiocresol (55 mg) in toluene over a period of 10 minutes, followed by stirring at the same temperature for 30 minutes.

Gas chromatographic assay gave the following optical isomer ratio: (+)-cis, 4.3%; (−)-cis, 6.9%; (+)-trans, 44.3%; and (−)-trans, 44.5%.

EXAMPLE 25

500 mg of (−)-cis-chrysanthemic acid and 48 mg of azobisisobutyronitrile were dissolved in 5 ml of toluene and thereto was added a solution of 1-butanethiol (40 mg) in toluene over a period of 10 minutes with stirring at 80° C., followed by stirring at the same temperature for 30 minutes.

Gas chromatographic assay gave the following optical isomer ratio: (+)-cis, 3.4%; (−)-cis, 45.0%; (+)-trans, 25.7%; and (−)-trans, 25.9%.

EXAMPLE 26

In a 50 ml flask, under nitrogen, 2.0 g of the same (−)-chrysanthemic acid as used in Example 21 and 0.2 g of azobisisobutyronitrile were dissolved in 10 ml of benzene and thereto was added dropwise a solution of thiobenzoic acid (0.25 g) in benzene with stirring at 75°–80° C., followed by stirring at the same temperature for 2 hours.

Then, a post-treatment similar to Example 21 was effected to obtain 1.74 g of chrysanthemic acid. Optical isomer ratio thereof was as follows: (+)-cis, 3.4%; (−)-cis, 3.7%; (+)-trans, 44.6%; and (−)-trans, 48.3%.

EXAMPLE 27

In a 50 ml flask, under nitrogen, 2.0 g of the same (−)-chrysanthemic acid as used in Example 21 and 0.46 g of tert-butyl perbenzoate were dissolved in 10 ml of benzene and thereto was added dropwise a solution of thioacetic acid (0.14 g) in benzene with stirring at 75°–80° C., followed by stirring at the same temperature for 2 hours.

Gas chromatographic analysis showed the following optical isomer ratio: (+)-cis, 3.2%; (−)-cis, 4.1%; (+)-trans, 42.5%; and (−)-trans, 50.2%.

EXAMPLE 28

In a 50 ml flask, under nitrogen, 2.0 g of methyl chrysanthemate (composition: (+)-cis, 0.6%; (−)-cis, 18.3%; (+)-trans, 2.7%: and (−)-trans, 78.4%) and 0.18 g of azobisisobutyronitrile were dissolved in 10 ml of benzene and thereto was added dropwise a solution of thiobenzoic acid (0.23 g) in benzene with stirring at 75°–80° C., and the reaction mixture was stirred at the same temperature for 1 hour.

Then, a post-treatment similar to Example 22 was effected to obtain 1.62 g of methyl chrysanthemate. Optical isomer ratio thereof was as follows: (+)-cis, 4.3%; (−)-cis, 4.3%; (+-trans, 42.7%; and (−)-trans, 48.7%.

EXAMPLE 29

In a 50 ml flask, under nitrogen, 2.0 g of the same (−)-chrysanthemic acid as used in Example 21 and 0.28 g of thiosalicylic acid were dissolved in benzene and thereto was added dropwise a solution of lauroyl peroxide (0.47 g) in benzene with stirring at 75°–80° C., followed by further stirring for 2 hours at the same temperature.

Then, optical isomer ratio thereof was determined by gas chromatography to obtain the following results: (+)-cis, 3.5%; (−)-cis, 3.4%; (+)-trans, 44.6%; and (−)-trans, 48.5%.

EXAMPLE 30

2.0 g of cis-chrysanthemic acid and 43 mg of benzoyl peroxide were dissolved in 20 ml of toluene and thereto was added dropwise a solution of bromine (28 mg) in carbon tetrachloride with stirring at 80° C. over a period of 20 minutes, and the reaction mixture was stirred at the same temperature for 20 minutes. Then, a post-treatment similar to Example 1 was effected to obtain 1.87 g of chrysanthemic acid. Gas chromatographic assay thereof showed the composition: cis, 5.9%; and trans, 94.1%.

EXAMPLE 31

2.0 g of cis-chrysanthemic acid and 23 mg of azobisisobutyronitrile were dissolved in 20 ml of toluene and thereto was added dropwise a solution of bromine (21 mg) in carbon tetrachloride with stirring at 80° C. over a period of 20 minutes. Thereafter, a treatment similar to Example 1 was carried out to obtain 1.91 g of chrysanthemic acid. Gas chromatographic assay thereof showed the composition: cis, 9.8% and trans, 90.2%.

EXAMPLE 32

10.0 g of chrysanthemic acid (composition: cis, 20.1% and trans, 79.9%) and 0.27 g of t-butyl hydroperoxide were dissolved in 20 ml of toluene and thereto was added dropwise a solution of bromine (0.95 g) in carbon tetrachloride with stirring at 80° C. over a period of 20 minutes. Thereafter, a post-treatment similar to Example 1 was effected to obtain 9.1 g of chrysanthemic acid.

Gas chromatographic assay gave the following results: cis, 6.3% and trans, 93.7%.

EXAMPLE 33

5.0 g of ethyl chrysanthemate (composition: cis, 20.1% and trans, 79.9%) and 0.49 g of benzoyl peroxide were dissolved in 20 ml of toluene and thereto was added dropwise a solution of bromine (0.41 g) in carbon tetrachloride with stirring at 80° C., and the reaction mixture was stirred for 0.5 hour at the same temperature. Then, a treatment similar to Example 8 was effected to obtain 4.1 g of ethyl chrysanthemate.

Gas chromatographic analysis gave the following result: cis, 7.6% and trans, 92.4%.

EXAMPLE 34

5.0 g of cis-chrysanthemic acid and 0.2 g of azobisisobutyronitrile were dissolved in 50 ml of toluene and thereto was added dropwise a solution of acetyl bromide (55 mg) in toluene with stirring at 80° C. over a period of 20 minutes. Then, the same treatment as in Example 1 was effected to obtain 4.6 g of chrysanthemic acid. The IR spectrum thereof was identical with that of chrysanthemic acid.

Gas chromatographic analysis gave the following result: cis, 9.9% and trans, 90.1%.

EXAMPLE 35

0.50 g of cis-chrysanthemic acid and 47 mg of azobisisobutyronitrile were dissolved in 10 ml of toluene. Thereto was added dropwise 59 mg of thionyl bromide with stirring at 80° C. and the reaction mixture was kept stirring for 20 minutes.

A treatment similar to Example 1 was effected to obtain 0.4 g of chrysanthemic acid. Isomer ratio was as follows: cis, 10.7% and trans, 89.3%.

EXAMPLE 36

0.32 g of cis-ethyl chrysanthemate and 30 mg of azobisisobutyronitrile were dissolved in 10 ml of toluene and thereto was added 49 mg of trimethylsilyl bromide and reaction mixture was stirred for 20 minutes. Isomer ratio of the reaction product was as follows: cis, 31.4% and trans, 68.6%.

EXAMPLE 37

1.0 g of cis-chrysanthemic acid and 48 mg of azobisisobutyronitrile were dissolved in 5 ml of toluene and thereto was added dropwise a solution of thiophenol (55 mg) in toluene with stirring at 80° C., followed by further stirring at the same temperature for 30 minutes. Then, isomer ratio was determined by gas chromatography to obtain the following results: cis, 10.4% and trans, 89.6%.

We claim:

1. A method for preparing racemized chrysanthemic acid or its ester by treating an optically active chrysanthemic acid or its ester having the formula:

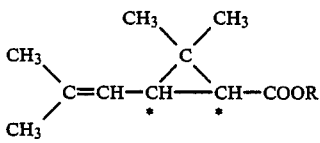

wherein R represents a hydrogen atom, an alkyl group of 1-20 carbon atoms, a cycloalkyl group of 3-20 carbon atoms of an aralkyl group of 7-20 carbon atoms and * mark represents asymmetric carbon atom, which comprises contacting with at least one compound selected from the group consisting of a carboxylic acid bromide, a silicon bromide, an S-bromine compound, an N-bromine compound, a halo-bromine compound and an SH compound in the presence of a peroxide or an azo compound.

2. A method according to claim 1 wherein the peroxide is selected from the group consisting of hydroperoxides, diacyl peroxides and peroxy esters.

3. A method according to claim 1 wherein the azo compound is selected from the group consisting of azonitriles and azo esters.

4. A method according to claim 1, 2 or 3 wherein the carboxylic acid bromides have 1-18 carbon atoms.

5. A method according to claim 1, 2 or 3 wherein the silicon bromide is selected from the group consisting of lower alkylsilyl bromide and silyl tetrabromide.

6. A method according to claim 1, 2 or 3 wherein the S-bromine compound is selected from the group consisting of thionyl bromide, sulfuryl bromide, arylsulfonyl bromide, arylsulfinyl bromide, lower alkylsulfonyl bromide, and alkyl sulfinyl bromide.

7. A method according to claim 1, 2 or 3 wherein the N-bromine compound is selected from the group consisting of N-bromoimide and N-bromoamide.

8. A method according to claim 1, 2 or 3 wherein the halo-bromine compound is selected from the group consisting of bromine and iodine bromide.

9. A method according to claim 1, 2 or 3 wherein the SH compound is selected from the group consisting of thiol, thiocarboxylic acid and dithio acid.

10. A method for conversion of a cis isomer or of a mixture of cis and trans isomers of chrysanthemic acid or its ester having the formula:

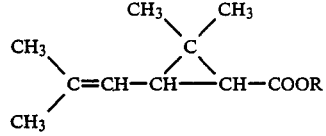

wherein R represents a hydrogen atom, an alkyl group of 1-20 carbon atoms, a cycloalkyl group of 3-20 carbon atoms or an aralkyl group of 7-20 carbon atoms, to the corresponding trans-chrysanthemic acid or its ester, which comprises contacting with at least one compound selected from the group consisting of a carboxylic acid bromide, a silicon bromide, an S-bromine compound, an N-bromine compound, a halo-bromine compound and an SH compound in the presence of a peroxide or an azo compound.

11. A method according to claim 10 wherein the peroxide is selected from the group consisting of hydroperoxides, diacyl peroxides and peroxy esters.

12. A method according to claim 10 wherein the azo compound is selected from the group consisting of azonitriles and azo esters.

13. A method according to claim 10, 11 or 12 wherein the carboxylic acid bromides have 1-18 carbon atoms.

14. A method according to claim 10, 11 or 12 wherein the silicon bromide is selected from the group consisting of lower alkylsilyl bromide and silyl tetrabromide.

15. A method according to claim 10, 11 or 12 wherein the S-bromine compound is selected from the group consisting of thionyl bromide, sulfuryl bromide, arylsulfonyl bromide, arylsulfinyl bromide, lower alkylsulfonyl bromide, and alkylsulfinyl bromide.

16. A method according to claim 10, 11 or 12 wherein the N-bromine compound is selected from the group consisting of N-bromoimide and N-bromoamide.

17. A method according to claim 10, 11 or 12 wherein the halo-bromine compound is selected from the group consisting of bromine and iodine bromide.

18. A method according to claim 10, 11 or 12 wherein the SH compound is selected from the group consisting of thiol, thiocarboxylic acid and dithio acid.

* * * * *